United States Patent

Andree et al.

Patent Number: 5,877,121
Date of Patent: Mar. 2, 1999

[54] SUBSTITUTED PYRIMIDIN(ETHI)ONES

[75] Inventors: Roland Andree; Mark Wilhelm Drewes, both of Langenfeld; Hans-Joachim Santel; Markus Dollinger, both of Leverkusen, all of Germany

[73] Assignee: Bayer Aktiengesellschaft, Leverkusen, Germany

[21] Appl. No.: 793,397

[22] PCT Filed: Aug. 21, 1995

[86] PCT No.: PCT/EP95/03314

§ 371 Date: Feb. 24, 1997

§ 102(e) Date: Feb. 24, 1997

[87] PCT Pub. No.: WO96/07647

PCT Pub. Date: Mar. 14, 1996

[30] Foreign Application Priority Data

Sep. 2, 1994 [DE] Germany .................. 44 31 218.0

[51] Int. Cl.$^6$ ................ C07D 239/36; C07D 239/40; A01N 43/54
[52] U.S. Cl. ............... 504/240; 504/242; 544/353; 544/319
[58] Field of Search ............... 504/240, 242; 544/253, 319

[56] References Cited

FOREIGN PATENT DOCUMENTS

| A 0 396 250 | 11/1990 | European Pat. Off. . |
| A 0 398 499 | 11/1990 | European Pat. Off. . |
| A 0 481 604 | 4/1992 | European Pat. Off. . |
| A 0 568 041 | 11/1993 | European Pat. Off. . |
| 1447108 | 8/1976 | United Kingdom . |

*Primary Examiner*—John M. Ford
*Attorney, Agent, or Firm*—Sprung Kramer Schaefer & Briscoe

[57] ABSTRACT

The invention relates to novel substituted pyrimidin(ethi) ones of the general formula (I)

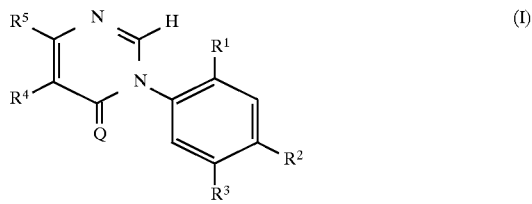

in which

Q, $R^1$, $R^2$, $R^3$, $R^4$ and $R^5$ have the meanings mentioned in the description, a process for their preparation and their use as herbicides.

13 Claims, No Drawings

SUBSTITUTED PYRIMIDIN(ETHI)ONES

The invention relates to novel substituted pyrimidin(ethi)ones, a process for their preparation and their use as herbicides.

Substituted pyrimidinones as potential herbicides already form the subject matter of one patent application, but they have hitherto not attained any major importance (cf. EP-A European Published Specification) 568041).

Novel substituted pyrimidin(ethi)ones of the general formula (I) have now been found

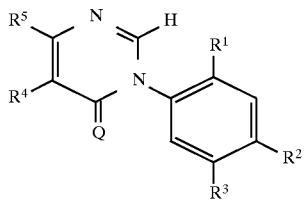

in which
Q represents oxygen or sulphur,
$R^1$ represents hydrogen, cyano, nitro, halogen, alkyl or halogenoalkyl,
$R^2$ represents cyano or thiocarbamoyl,
$R^3$ represents the following grouping

where
$A^1$ represents a single bond, or oxygen, sulphur, —SO—, —SO$_2$—, —CO— or the grouping —N—$A^4$— where $A^4$ represents hydrogen, hydroxyl, amino, alkyl, alkoxy, aryl, alkylcarbonyl, alkoxycarbonyl, alkylsulphonyl, arylcarbonyl or arylsulphonyl, or
$A^1$ also represents respectively optionally substituted alkanediyl, alkenediyl, azaalkenediyl, alkinediyl, cycloalkanediyl, cycloalkenediyl or arenediyl,
$A^2$ represents a single bond, or oxygen, sulphur, —SO—, —SO$_2$—, —CO— or the grouping —N—$A^4$— where $A^4$ represents hydrogen, alkyl, aryl, alkylcarbonyl, alkylsulphonyl or arylsulphonyl,
$A^2$ also represents respectively optionally substituted alkanediyl, alkenediyl, azaalkenediyl, alkinediyl, cycloalkanediyl, cycloalkenediyl or arenediyl, and
$A^3$ represents hydrogen, hydroxyl, mercapto, amino, cyano, isocyano, thiocyanato, nitro, carboxyl, carbamoyl, thiocarbamoyl, sulpho, chlorosulphonyl, halogen or respectively optionally substituted alkyl, alkoxy, alkylthio, alkylsulphinyl, alkylsulphonyl, alkylamino, dialkylamino, alkoxycarbonyl, dialkoxy(thio)phosphoryl, alkenyl, alkenyloxy, alkenylamino, alkylideneamino, alkenyloxycarbonyl, alkinyl, alkinyloxy, alkinylamino, alkinyloxycarbonyl, cycloalkyl, cycloalkyloxy, cycloalkylalkyl, cycloalkylalkoxy, cycloalkylideneamino, cycloalkyloxycarbonyl, cycloalkylalkoxycarbonyl, aryl, aryloxy, arylalkyl, arylalkoxy, aryloxycarbonyl, arylalkoxycarbonyl, heterocyclyl, heterocyclylalkyl, heterocyclylalkoxy or heterocyclylalkoxycarbonyl,
$R^4$ represents hydrogen, halogen, alkyl or halogenoalkyl, and
$R^5$ represents alkyl or halogenoalkyl or together with $R^4$ represents alkanediyl.

The novel substituted pyrimidin(ethi)ones of the general formula (I) are obtained by reacting halogenoarenes of the general formula (II)

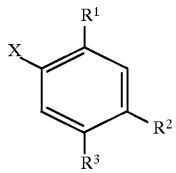

in which
$R^1$, $R^2$ and $R^3$ have the abovementioned meanings, and
X represents halogen,
with pyrimidin(ethi)ones of the general formula (III)

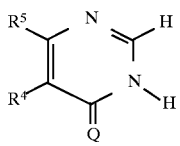

in which
Q, $R^4$ and $R^5$ have the abovementioned meanings,
if necessary in the presence of an acid acceptor and if necessary in the presence of a diluent, and optionally subjecting, in the resulting compounds of the formula (I), the groups designated Q, $R^1$, $R^2$, $R^3$, $R^4$ and $R^5$ in a conventional manner to further chemical modifications within the purview of the radical definitions given above.

The novel substituted pyrimidin(ethi)ones of the general formula (I) are distinguished by strong and selective herbicidal activity.

In the definitions, the saturated or unsaturated hydrocarbon chains, such as alkyl, alkanediyl, alkenyl or alkinyl—also when attached to heteroatoms, as in alkoxy, alkylthio or alkylamino—are in each case straight-chain or branched.

Halogen represents in general fluorine, chlorine, bromine or iodine, preferably fluorine, chlorine or bromine, in particular fluorine or chlorine.

The invention preferably relates to compounds of the formula (I) in which
Q represents oxygen or sulphur,
$R^1$ represents hydrogen, cyano, nitro, fluorine, chlorine, bromine or optionally fluorine- and/or chlorine-substituted alkyl having 1 to 4 carbon atoms,
$R^2$ represents cyano or thiocarbamoyl,
$R^3$ represents the following grouping

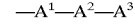

in which
$A^1$ represents a single bond, or oxygen, sulphur, —SO—, —SO$_2$—, —CO— or the grouping —N—$A^4$— where $A^4$ represents hydrogen, hydroxyl, amino, $C_1$–$C_4$-alkyl, $C_1$–$C_4$-alkoxy, phenyl, $C_1$–$C_4$-alkylcarbonyl, $C_1$–$C_4$-alkoxycarbonyl, $C_1$–$C_4$-alkylsulphonyl, phenylcarbonyl or phenylsulphonyl, or
$A^1$ also represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene,
$A^2$ represents a single bond, or oxygen, sulphur, —SO—, —SO$_2$—, —CO— or the grouping —N—$A^4$— where $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl,
$A^2$ also represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, $A^3$ represents hydrogen, hydroxyl, mercapto, amino, cyano, isocyano, thiocyanato, nitro, carboxyl, carbamoyl, thiocarbamoyl, sulpho, chlorosulphonyl, halogen or respectively optionally halogen- or $C_1$–$C_4$-alkoxy-substituted alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups, $A^3$ also represents respectively optionally halogen-substituted alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups, $A^3$ also represents respectively optionally halogen-, cyano-, carboxyl-, $C_1$–$C_4$-alkyl- and/or $C_1$–$C_4$-alkoxycarbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and optionally 1 to 4 carbon atoms in the alkyl groups, or $A^3$ also represents respectively optionally nitro-, cyano-, carboxyl-, halogen- $C_1$–$C_4$-alkyl-, $C_1$–$C_4$-halogenoalkyl-, $C_1$–$C_4$-alkyloxy-, $C_1$–$C_4$-halogenoalkyloxy- and/or $C_1$–$C_4$-alkoxycarbonyl-substituted phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, (respectively optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazol-$C_1$–$C_4$-alkyl, thiazol-$C_1$–$C_4$-alkyl, pyridinyl-$C_1$–$C_4$-alkyl, pyrimidinyl-$C_1$–$C_4$-alkyl, pyrazolylmethoxy, furylmethoxy, or perhydropyranylmethoxy or pyridylmethoxy, $R^4$ represents hydrogen, fluorine, chlorine or bromine, or optionally fluorine- and/or chlorine-substituted alkyl having 1 to 4 carbon atoms, and $R^5$ represents optionally fluorine- and/or chlorine-substituted alkyl having 1 to 4 carbon atoms or together with $R^4$ represents $C_3$–$C_4$-alkanediyl.

The invention in particular relates to compounds of the formula (I) in which $R^1$ represents hydrogen, fluorine or chlorine, $R^2$ represents cyano or thiocarbamoyl, $R^3$ represents the following grouping

—$A^1$—$A^2$—$A^3$ in which $A^1$ represents a single bond, or oxygen, sulphur, —SO—, —$SO_2$—, —CO— or the grouping —N—$A^4$— where $A^4$ represents hydrogen, hydroxyl, methyl, ethyl, n- or i-propyl, methoxy, ethoxy, n- or i-propoxy, methylsulphonyl or ethylsulphonyl, or $A^1$ also represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^2$ represents a single bond, or oxygen, sulphur, —SO—, —$SO_2$—, —CO— or the grouping —N—$A^4$— where $A^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, or $A^2$ also represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^3$ represents hydrogen, hydroxyl, mercapto, amino, cyano, isocyano, thiocyanato, nitro, carboxyl, carbamoyl, sulpho, fluorine, chlorine, bromine, or respectively optionally fluorine-, chlorine-, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphonyl, ethylsulphonyl, n- or i-propylsulphinyl, methylsulphonyl, ethylsulphonyl, n- or i- propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, $A^3$ also represents respectively optionally fluorine- or chlorine-substituted propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, $A^3$ also represents respectively optionally fluorine-, chlorine-, cyano-, carboxyl-, methyl-, ethyl-, n- or i-propyl-, methoxycarbonyl- or ethoxycarbonyl-substituted cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexylcarbonyl, cyclopentylmethoxycarbonyl or cyclohexylmethoxycarbonyl, or $A^3$ also represents respectively optionally nitro-, cyano-, carboxyl-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methoxycarbonyl- and/or ethoxycarbonyl-substituted phenyl, phenyloxy, benzyl, phenylethyl, benzyloxy, phenyloxycarbonyl, benzyloxycarbonyl, (respectively optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolmethyl, thiazolmethyl, pyridinylmethyl, pyrimidinylmethyl, pyrazolylmethoxy, furylmethoxy or pyridylmethoxy, $R^4$ represents hydrogen, fluorine, chlorine, bromine or respectively optionally fluorine- and/or chlorine-substituted methyl or ethyl, and $R^5$ represents respectively optionally fluorine- and/or chlorine-substituted methyl or ethyl.

The above-listed general radical definitions, or those listed in preference ranges, are valid both for the end products of the formula (I) and also, in a corresponding manner, for the starting materials or intermediates which are required in each case for the preparation. These radical definitions can be combined at will among themselves, that is between the given preferred ranges as well.

If for example 5-chloro-6-trifluoromethyl-pyrimidin-4-one and 4,5-difluoro-2-methoxy-benzonitrile are used as starting materials, then the course of the reaction in the process according to the invention can be illustrated by the following formula scheme:

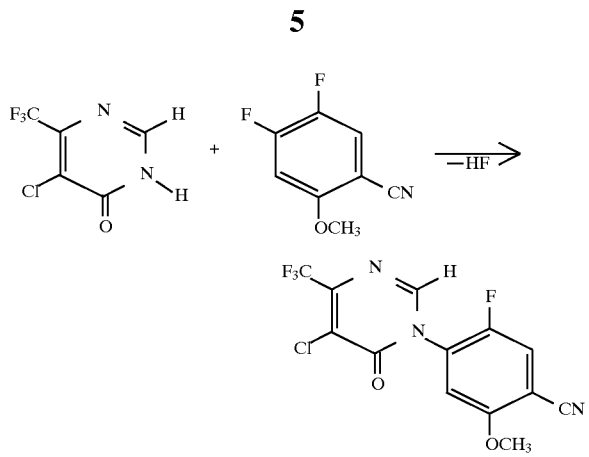

The halogenoarenes to be used as starting materials in the process according to the invention for preparing the compounds of the general formuls (I) are defined in a general way by the formula (II). In the formula (II), $R^1$, $R^2$ and $R^3$ preferably or in particular have those meanings which have already been indicated above, in connection with the description of compounds of the formula (I), as being preferred or particularly preferred for $R^1$, $R^2$ and $R^3$; X preferably represents fluorine, chlorine or bromine, in particular fluorine or chlorine.

The starting materials of the formula (II) are known and/or can be prepared by known procedures (cf. EP-A (European Published Specification) 431373, EP-A (European Published Specification) 441004, EP-A (European Published Specification) 597360).

The pyrimidin(ethi)ones to be further used as starting materials in the process according to the invention for preparing the compounds of the general formula (I) are defined in a general way by the formula (III). In formula (III), Q, $R^4$ and $R^5$ preferably or in particular have those meanings which have already been indicated above, in connection with the description of the compounds of the formula (I), as being preferred or particularly preferred for Q, $R^4$ and $R^5$.

The starting materials of the formula (III) are known and/or can be prepared by known procedures (cf. EP-A European Published Specification) 357201, EP-A European Published Specification) 395977, Preparation Examples).

The process according to the invention is preferably carried out in the presence of a suitable acid acceptor. Suitable acid acceptors are all customary inorganic or organic bases. These are for example alkali metal or alkaline earth metal hydrides, hydroxides, amides, alcoholates, acetates, carbonates or hydrogen carbonates, such as, for example, lithium hydride, sodium hydride, potassium hydride or calcium hydride, lithium amide, sodium amide or potassium amide, sodium methylate or potassium methylate, sodium ethylate or potassium ethylate, sodium propylate or potassium propylate, aluminium isopropylate, sodium tert-butylate or potassium tert-butylate, sodium hydroxide or potassium hydroxide, ammonium hydroxide, sodium acetate, potassium acetate or calcium acetate, ammonium acetate, sodium carbonate, potassium carbonate or calcium carbonate, ammonium carbonate, sodium hydrogen carbonate or potassium hydrogen carbonate, and also basic organic nitrogen compounds such as trimethylamine, triethylamine, tripropylamine, tributylamine, ethyl-diisopropylamine, N,N-dimethylcyclohexylamine, dicyclohexylamine, ethyl-dicyclohexylamine, N,N-dimethylaniline, N,N-dimethylbenzylamine, pyridine, 2-methyl-, 3-methyl- and 4-methylpyridine, 2,4-dimethyl-, 2,6-dimethyl-, 3,4-dimethyl- and 3,5-dimethylpyridine, 5-ethyl-2-methyl-pyridine, N-methylpiperidine, N,N-dimethylaminopyridine, diazabicyclooctane (DABCO), diazabicyclononene (DBN) or diazabicycloundecane (DBU).

Suitable diluents for carrying out the process according to the invention are the customary organic solvents. These are in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, their mixtures with water or pure water.

In the practice of the process according to the invention, the reaction temperatures may be varied over a relatively wide range. In general, temperatures of between –20° C. and +150° C., preferably temperatures of between –10° C. and +120° C., in particular temperatures of between 0° C. and 100° C., are employed.

The process according to the invention is generally carried out under atmospheric pressure. However, it is also possible to operate under elevated or reduced pressure—in general between 0.1 bar and 10 bar.

The starting materials required in each case to carry out the process according to the invention are generally employed in approximately equimolar quantities. However, it is also possible to use one of the two components employed in each case in a relatively large excess. The reactions are generally carried out in a suitable diluent, and the reaction mixture is stirred for several hours at the temperature required in each case. In the process according to the invention, work-up takes place in each case according to customary methods (cf. the Preparation Examples).

The active compounds according to the invention can be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:
Dicotyledon Weeds of the Genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.
Dicotyledon Crops of the Genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.
Monocotyledon Weeds of the Genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon Crops of the Genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds of the formula (I) according to the invention are suitable in particular for the selective control of dicotyledon weeds in monocotyledon and dicotyledon crops, both pre- and post-emergence.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foamformers are: for example non-ionic and anionic emulsifiers, such as poly-oxyethylene fatty acid esters, polyoxyethylene fatty alcohol ethers, for example alkylaryl polyglycol ethers, alkylsulphonates, alkyl sulphates, arylsulphonates and protein hydrolyzates; suitable dispersants are: for example lignin-sulphite waste liquors and methylcellulose.

Adhesives such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil; dichlobenil and ioxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifensulphuronmethyl, triasulphuron and tribenuronmethyl; thiocarbamates such as, for example, butylate, cycloate, di-allate, EPTC, esprocarb, molinate, prosulphocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds such as fungicides, insecticides, acaricides, nematicides, bird repellants, plant nutrients and soil conditioners, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 5 g and 5 kg of active compound per hectare of soil surface, preferably between 10 g and 2 kg per ha.

The preparation and use of the active compounds according to the invention can be seen from the examples which follow.

PREPARATION EXAMPLES

Example 1

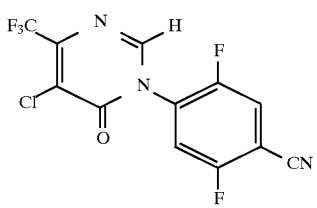

A mixture of 3.0 g (18.3 mmol) of 6-trifluoromethyl-pyrimidin-4-one, 2.5 g (18.3 mmol) of potassium carbonate and 50 ml of dimethyl sulphoxide is stirred at 20° C. for 15 hours. 2.9 g (18.3 mmol) of 2,4,5-trifluoro-benzonitrile are then added, and the mixture is stirred at 60° C. for 8 hours. After concentrating the mixture under reduced pressure, the residue is mixed with water and the crystalline product is isolated by filtration.

2.7 g (49% of theory) of 3-(4-cyano-2,5-difluoro-phenyl)-6-trifluoromethyl-pyrimidin-4-one of melting point 95° C. are obtained.

Example 2

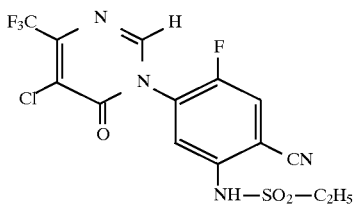

A mixture of 4.3 g (14.3 mmol) of 3-(4-cyano-2,5-difluoro-phenyl)-6-trifluoromethyl-pyrimidin-4-one (cf. Example 1), 1.6 g (14.3 mmol) of ethanesulphonamide, 2.0 g (14.3 mmol) of potassium carbonate and 50 ml of dimethyl sulphoxide is stirred at 60° C. for 6 hours and then concentrated under reduced pressure. The residue is taken up in water and, after acidification, shaken with methylene chloride. The organic phase is dried with sodium sulphate and filtered. The filtrate is concentrated, and the crude product obtained as residue is purified by column chromatography (silica gel, ethyl acetate/chloroform, 1:1 by volume). 100 mg (2% of theory) of 3-(4-cyano-5-ethylsulphonylamino-2-fluoro-phenyl)-6-trifluoromethyl-pyrimidin-4-one of melting point 170° C. are obtained.

The methods of Example 1 and 2 and the general description of the process according to the invention can also be used to prepare for example the compounds of the formula (I) listed in Table 1 below:

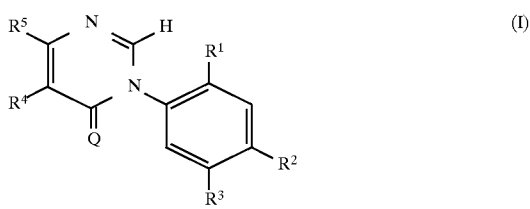

TABLE 1

Examples of compounds of the formula (I)

| Ex. No. | Q | $R^1$ | $R^2$ | $R^3$ | $R^4$ | $R^5$ | Melting point (°C.) |
|---|---|---|---|---|---|---|---|
| 3 | O | F | CN | $NHSO_2CH_3$ | H | $CH_3$ | |
| 4 | O | H | CN | $NHSO_2CH_3$ | H | $CF_3$ | |
| 5 | O | F | CN | $NHSO_2CH_3$ | H | $CF_3$ | |
| 6 | O | H | $CSNH_2$ | $NHSO_2C_2H_5$ | H | $CF_3$ | |
| 7 | O | F | $CSNH_2$ | $NHSO_2C_2H_5$ | H | $CF_3$ | |
| 8 | S | F | CN | $NHSO_2C_2H_5$ | H | $CF_3$ | |
| 9 | O | F | CN | $NHSO_2C_3H_7$ | H | $CHF_2$ | |
| 10 | O | F | CN | $NHSO_2C_4H_9$ | H | $CF_2Cl$ | |
| 11 | O | F | CN | $NHSO_2C_2H_5$ | H | $C_2F_5$ | |
| 12 | O | H | $CSNH_2$ | $NHSO_2CH_3$ | $CH_3$ | $CF_3$ | |
| 13 | O | F | CN | $OCH_3$ | H | $CF_3$ | |
| 14 | O | F | $CSNH_2$ | $OC_2H_5$ | $CH_3$ | $CF_3$ | |
| 15 | S | H | CN | O—CH—C≡CH<br>      \|<br>     $CH_3$ | H | $CF_3$ | |
| 16 | O | F | CN | $NH_2$ | H | $CF_3$ | |
| 17 | O | F | CN | $NH-CH_2-COOEt$ | H | $CF_3$ | |
| 18 | O | F | CN | CHO | H | $CF_3$ | |
| 19 | O | H | CN | COOEt | H | $CF_3$ | |
| 20 | O | F | CN | $CH=CH-COOEt$ | H | $CF_3$ | |
| 21 | O | F | CN | $S-CH_2-COOMe$ | H | $CF_3$ | |
| 22 | O | F | CN | $S-CH_3$ | H | $CF_2Cl$ | |
| 23 | O | F | CN | $SO_2NH_2$ | H | $CF_3$ | |
| 24 | O | F | CN | $NO_2$ | H | $CF_3$ | |
| 25 | O | F | CN | OH | H | $CF_3$ | |
| 26 | O | F | CN | SH | H | $CF_3$ | |
| 27 | O | F | CN | $-CH_2-COOEt$ | H | $CF_3$ | |
| 28 | O | F | CN | —CH—COOEt<br>    \|<br>   $CH_3$ | H | $CF_3$ | |

Starting Materials of the Formula (III)

Example (III-1)

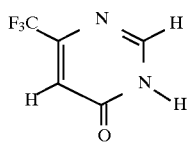

A mixture of 30 g (288 mmol) of formamidine acetate, 35.4 g (192 mmol) of ethyl trifluoroacetate, 24.5 g (230 mmol) of sodium carbonate and 250 ml of methanol is stirred at 60° C. for 20 hours; after cooling, the pH of the mixture is then adjusted to about 3 by addition of 56 g of conc. hydrochloric acid and the crystalline product is isolated by filtration.

22.8 g (48% of theory) of 6-trifluoromethyl-pyrimidin-4-one of melting point 157° C. are obtained.

Example A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example the compound obtained by Preparation Example 2 is, when applied in amounts of 15 g/ha, very well tolerated by crops, such as, for example, wheat and soya (0%), and exhibits strong activity against weeds (Abuliton 90%), Amaranthus (80%), Ambrosia (100%), Galinsoga (100%), Solanum (80%) and Viola (80%).

We claim:

1. A compound of the formula (I)

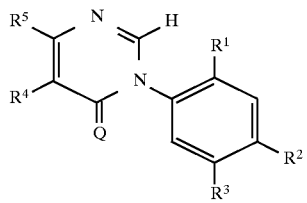

in which

Q represents oxygen or sulphur, $R^1$ represents hydrogen, cyano, nitro, fluorine, chlorine, bromine or optionally fluorine- and/or chlorine-substituted alkyl having 1 to 4 carbon atoms, $R^2$ represents cyano or thiocarbamoyl, $R^3$ represents the following grouping

in which $A^1$ represents a single bond, or oxygen, sulphur, —SO—, —SO$_2$—, —CO— or the grouping —N—$A^4$— where $A^4$ represents hydrogen, hydroxyl, amino, $C_1$–$C_4$-alkyl, $C_1$–$C_4$-alkoxy, phenyl, $C_1$–$C_4$-alkylcarbonyl, $C_1$–$C_4$-alkoxycarbonyl, $C_1$–$C_4$-alkylsulphonyl, phenylcarbonyl or phenylsulphonyl, or $A^1$ also represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, $A^2$ represents a single bond, or oxygen, sulphur, —SO—, —SO$_2$—, —CO— or the grouping —N—$A^4$— where $A^4$ represents hydrogen, hydroxyl, $C_1$–$C_4$-alkyl, $C_1$–$C_4$-alkoxy, phenyl, $C_1$–$C_4$-alkylsulphonyl or phenylsulphonyl, $A^2$ also represents respectively optionally fluorine-, chlorine- or bromine-substituted $C_1$–$C_6$-alkanediyl, $C_2$–$C_6$-alkenediyl, $C_2$–$C_6$-azaalkenediyl, $C_2$–$C_6$-alkinediyl, $C_3$–$C_6$-cycloalkanediyl, $C_3$–$C_6$-cycloalkenediyl or phenylene, $A^3$ represents hydrogen, hydroxyl, mercapto, amino, cyano, isocyano, thiocyanato, nitro, carboxyl, carbamoyl, thiocarbamoyl, sulpho, chlorosulphonyl, halogen or respectively optionally halogen- or $C_1$–$C_4$-alkoxy-substituted alkyl, alkoxy, alkylthio, alkylsulphinyl, alkylsulphonyl, alkylamino, dialkylamino, alkoxycarbonyl or dialkoxy(thio)phosphoryl having in each case 1 to 6 carbon atoms in the alkyl groups, $A^3$ also represents respectively optionally halogen-substituted alkenyl, alkenyloxy, alkenylamino, alkylideneamino, alkenyloxycarbonyl, alkinyl, alkinyloxy, alkinylamino or alkinyloxycarbonyl having in each case 2 to 6 carbon atoms in the alkenyl, alkylidene or alkinyl groups, $A^3$ also represents respectively optionally halogen-, cyano-, carboxyl-, $C_1$–$C_4$-alkyl- and/or $C_1$–$C_4$-alkoxycarbonyl-substituted cycloalkyl, cycloalkyloxy, cycloalkylalkyl, cycloalkylalkoxy, cycloalkylideneamino, cycloalkyloxycarbonyl or cycloalkylalkoxycarbonyl having in each case 3 to 6 carbon atoms in the cycloalkyl groups and optionally 1 to 4 carbon atoms in the alkyl groups, or $A^3$ also represents respectively optionally nitro-, cyano-, carboxyl-, halogen- $C_1$–$C_4$-alkyl-, $C_1$–$C_4$-halogenoalkyl-, $C_1$–$C_4$-alkyloxy-, $C_1$–$C_4$-halogenoalkyloxy- and/or $C_1$–$C_4$-alkoxycarbonyl-substituted phenyl, phenyloxy, phenyl-$C_1$–$C_4$-alkyl, phenyl-$C_1$–$C_4$-alkoxy, phenyloxycarbonyl or phenyl-$C_1$–$C_4$-alkoxycarbonyl, (respectively optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolyl-$C_1$–$C_4$-alkyl, furyl-$C_1$–$C_4$-alkyl, thienyl-$C_1$–$C_4$-alkyl, oxazolyl-$C_1$–$C_4$-alkyl, isoxazole-$C_1$–$C_4$-alkyl, thiazole-$C_1$–$C_4$-alkyl, pyridinyl-$C_1$–$C_4$-alkyl, pyrimidinyl-$C_1$–$C_4$-alkyl, pyrazolylmethoxy, furylmethoxy, or perhydropyranylmethoxy or pyridylmethoxy, $R^4$ represents hydrogen, fluorine, chlorine or bromine, or optionally fluorine- and/or chlorine-substituted alkyl having 1 to 4 carbon atoms, and $R^5$ represents optionally fluorine- and/or chlorine-substituted alkyl having 1 to 4 carbon atoms or together with $R^4$ represents $C_3$–$C_4$-alkanediyl.

2. A compound of the formula (I) according to claim 1, wherein $R^1$ represents hydrogen, fluorine or chlorine, $R^2$ represents cyano or thiocarbamoyl, $R^3$ represents the following grouping

in which $A^1$ represents a single bond, or oxygen, sulphur, —SO—, —SO$_2$—, —CO— or the grouping —N—$A^4$— where $A^4$ represents hydrogen, hydroxyl, methyl, ethyl, n- or i-propyl, methoxy, ethoxy, n- or i-propoxy, methylsulphonyl or ethylsulphonyl, or $A^1$ also represents methylene, ethane-1,1-diyl, ethane-1,2-diyl, propane-1,1-diyl, propane-1,2-diyl, propane-1, 3-diyl, ethene-1,2-diyl, propene-1,2-diyl, propene-1,3-diyl, ethine-1,2-diyl, propine-1,2-diyl or propine-1,3-diyl, $A^2$ represents a single bond, or oxygen, sulphur, —SO—, —$SO_2$—, —CO— or the grouping —N—$A^4$— where $A^4$ represents hydrogen, hydroxyl, methyl, ethyl, n- or i-propyl, methoxy, ethoxy, n- or i-propoxy, methylsulphonyl, ethylsulphonyl, n- or i-propylsulphonyl or phenylsulphonyl, or $A^2$ also represents methylene, ethane-1,1-diyl, ethane-1,2-diyl, propane-1,1-diyl, propane-1,2-diyl, propane-1,3-diyl, ethene-1,2-diyl, propene-1,2-diyl, propene-1,3-diyl, ethine-1,2-diyl, propine-1,2-diyl or propine-1,3-diyl, $A^3$ represents hydrogen, hydroxyl, mercapto, amino, cyano, isocyano, thiocyanato, nitro, carboxyl, carbamoyl, sulpho, fluorine, chlorine, bromine, or respectively optionally fluorine-, chlorine-, methoxy- or ethoxy-substituted methyl, ethyl, n- or i-propyl, n-, i-, s- or t-butyl, n-, i-, s- or t-pentyl, methoxy, ethoxy, n- or i-propoxy, n-, i-, s- or t-butoxy, n-, i-, s- or t-pentyloxy, methylthio, ethylthio, n- or i-propylthio, n-, i-, s- or t-butylthio, methylsulphonyl, ethylsulphonyl, n- or i-propylsulphonyl, methylsulphonyl, ethylsulphonyl, n- or i-propylsulphonyl, methylamino, ethylamino, n- or i-propylamino, n-, i-, s- or t-butylamino, dimethylamino, diethylamino, methoxycarbonyl, ethoxycarbonyl, n- or i-propoxycarbonyl, dimethoxyphosphoryl, diethoxyphosphoryl, dipropoxyphosphoryl or diisopropoxyphosphoryl, $A^3$ also represents respectively optionally fluorine- or chlorine-substituted propenyl, butenyl, propenyloxy, butenyloxy, propenylamino, butenylamino, propylideneamino, butylideneamino, propenyloxycarbonyl, butenyloxycarbonyl, propinyl, butinyl, propinyloxy, butinyloxy, propinylamino, butinylamino, propinyloxycarbonyl or butinyloxycarbonyl, $A^3$ also represents respectively optionally fluorine-, chlorine-, cyano-, carboxyl-, methyl-, ethyl-, n- or i-propyl-, methoxycarbonyl- or ethoxycarbonyl-substituted cyclopropyl, cyclobutyl, cyclopentyl, cyclohexyl, cyclopropyloxy, cyclobutyloxy, cyclopentyloxy, cyclohexyloxy, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopentylideneamino, cyclohexylideneamino, cyclopentyloxycarbonyl, cyclohexylcarbonyl, cyclopentylmethoxycarbonyl or cyclohexylmethoxycarbonyl, or $A^3$ also represents respectively optionally nitro-, cyano-, carboxyl-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methoxycarbonyl- and/or ethoxycarbonyl-substituted phenyl, phenyloxy, benzyl, phenylethyl, benzyloxy, phenyloxycarbonyl, benzyloxycarbonyl, (respectively optionally fully or partially hydrogenated) pyrrolyl, pyrazolyl, imidazolyl, triazolyl, furyl, thienyl, oxazolyl, isoxazolyl, thiazolyl, isothiazolyl, oxadiazolyl, thiadiazolyl, pyridinyl, pyrimidinyl, triazinyl, pyrazolylmethyl, furylmethyl, thienylmethyl, oxazolylmethyl, isoxazolmethyl, thiazolmethyl, pyridinylmethyl, pyrimidinylmethyl, pyrazolylmethoxy, furylmethoxy or pyridylmethoxy, $R^4$ represents hydrogen, fluorine, chlorine, bromine or respectively optionally fluorine- and/or chlorine-substituted methyl or ethyl, and $R^5$ represents respectively optionally fluorine- and/or chlorine-substituted methyl or ethyl.

3. A compound of the formula (I) according to claim 1, wherein $R^1$ represents fluorine or chlorine.

4. A compound of the formula (I) according to claim 1, wherein $R^2$ represents cyano.

5. A compound of the formula (I) according to claim 1, wherein $R^3$ represents halogen or $NHSO_2$—($C_1$–$C_6$-Alkyl).

6. A compound of the formula (I) according to claim 1, wherein $R^5$ represents fluorine- and/or chlorine-substituted alkyl.

7. A compound of the formula (I) according to claim 1, wherein $R^1$ represents hydrogen.

8. A compound of the formula (I) according to claim 1, wherein $R^2$ represents thiocarbamoyl.

9. A compound of the formula (I) according to claim 1, wherein $R^4$ represents hydrogen.

10. A process for preparing compounds of the formula (I)

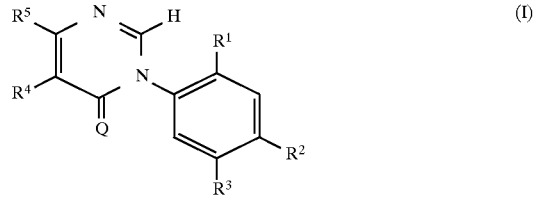

in which

Q, $R^1$, $R^2$, $R^3$, $R^4$ and $R^5$ have the meanings as set forth in claim 1, wherein compounds of the formula (II)

in which x represents halogen, are reacted with pyriridin(ethi)ones of the formula (III)

optionally in the presence of an acid acceptor.

11. A method for the control of undesired plants comprising allowing an effective amount of one or more compound(s) according to claim 1 to act on plants and/or their habitat.

12. Herbicidal compositions comprising at least one or more compound(s) according to claim 1 in combination with an inert carrier.

13. Herbicidal compositions according to claim 12 which further contain extenders and/or surface-active agents.

* * * * *